(12) United States Patent
Hawkins

(10) Patent No.: US 8,747,445 B2
(45) Date of Patent: Jun. 10, 2014

(54) SPINAL FIXATION DEVICE

(75) Inventor: Nathaniel E. Hawkins, Chatham, NJ (US)

(73) Assignee: EBI, LLC, Parsippany, NJ (US)

(*) Notice: Subject to any disclaimer, the term of this patent is extended or adjusted under 35 U.S.C. 154(b) by 2023 days.

(21) Appl. No.: 11/623,170

(22) Filed: Jan. 15, 2007

(65) Prior Publication Data
US 2008/0172096 A1 Jul. 17, 2008

(51) Int. Cl.
*A61B 17/86* (2006.01)
(52) U.S. Cl.
USPC ........... 606/305; 606/304; 606/306; 606/308
(58) Field of Classification Search
USPC ................................. 606/304–308
See application file for complete search history.

(56) References Cited

U.S. PATENT DOCUMENTS

| | | | |
|---|---|---|---|
| 4,763,644 A | 8/1988 | Webb | |
| 5,005,562 A | 4/1991 | Cotrel | |
| 5,176,680 A | 1/1993 | Vignaud et al. | |
| 5,352,226 A | 10/1994 | Lin | |
| 5,437,669 A | 8/1995 | Yuan et al. | |
| 5,509,900 A * | 4/1996 | Kirkman | 604/104 |
| 5,520,689 A | 5/1996 | Schlapfer et al. | |
| 5,536,268 A | 7/1996 | Griss | |
| 5,910,142 A | 6/1999 | Tatar | |
| 5,938,663 A | 8/1999 | Petreto | |
| 5,984,923 A | 11/1999 | Breard | |
| 6,077,262 A | 6/2000 | Schlapfer et al. | |
| 6,224,598 B1 | 5/2001 | Jackson | |
| 6,296,642 B1 | 10/2001 | Morrison et al. | |
| 6,565,565 B1 | 5/2003 | Yuan et al. | |
| 6,660,004 B2 | 12/2003 | Barker et al. | |
| 6,726,689 B2 | 4/2004 | Jackson | |
| 6,783,527 B2 | 8/2004 | Drewry et al. | |
| 6,896,677 B1 | 5/2005 | Lin | |
| 6,997,927 B2 | 2/2006 | Jackson | |
| 7,008,423 B2 | 3/2006 | Assaker et al. | |
| 7,083,621 B2 | 8/2006 | Shaolian et al. | |
| 2004/0167523 A1 | 8/2004 | Jackson | |
| 2004/0167524 A1 | 8/2004 | Jackson | |

(Continued)

FOREIGN PATENT DOCUMENTS

FR 2786088 5/2000

OTHER PUBLICATIONS

PCT International Search Report and the Written Opinion of the International Searching Authority mailed Jun. 9, 2008 for International Application No. PCT/US2008/000389.

*Primary Examiner* — Eduardo C Robert
*Assistant Examiner* — Julianna N Harvey
(74) *Attorney, Agent, or Firm* — Harness, Dickey

(57) ABSTRACT

An enclosure device connecting a pedicle fixation device with an elongated spinal fixation member. The enclosure device can include an enclosure member and an elongated guide member affixed to the enclosure member and defining a fracture region for breaking off the guide member from the enclosure member. The enclosure member can have a spherical outer surface rotatably received within a receiver portion of the pedicle fixation device. The enclosure member can include an internal bore capable of slidably receiving the fixation member.

19 Claims, 4 Drawing Sheets

(56) References Cited

U.S. PATENT DOCUMENTS

| | | |
|---|---|---|
| 2004/0172025 A1 | 9/2004 | Drewry et al. |
| 2004/0215190 A1* | 10/2004 | Nguyen et al. ............... 606/61 |
| 2005/0010220 A1 | 1/2005 | Casutt et al. |
| 2005/0240180 A1 | 10/2005 | Vienney et al. |
| 2005/0261687 A1* | 11/2005 | Garamszegi et al. ........... 606/61 |
| 2006/0084990 A1* | 4/2006 | Gournay et al. ................ 606/61 |
| 2006/0149232 A1 | 7/2006 | Sasing |
| 2006/0241595 A1 | 10/2006 | Molz et al. |

* cited by examiner

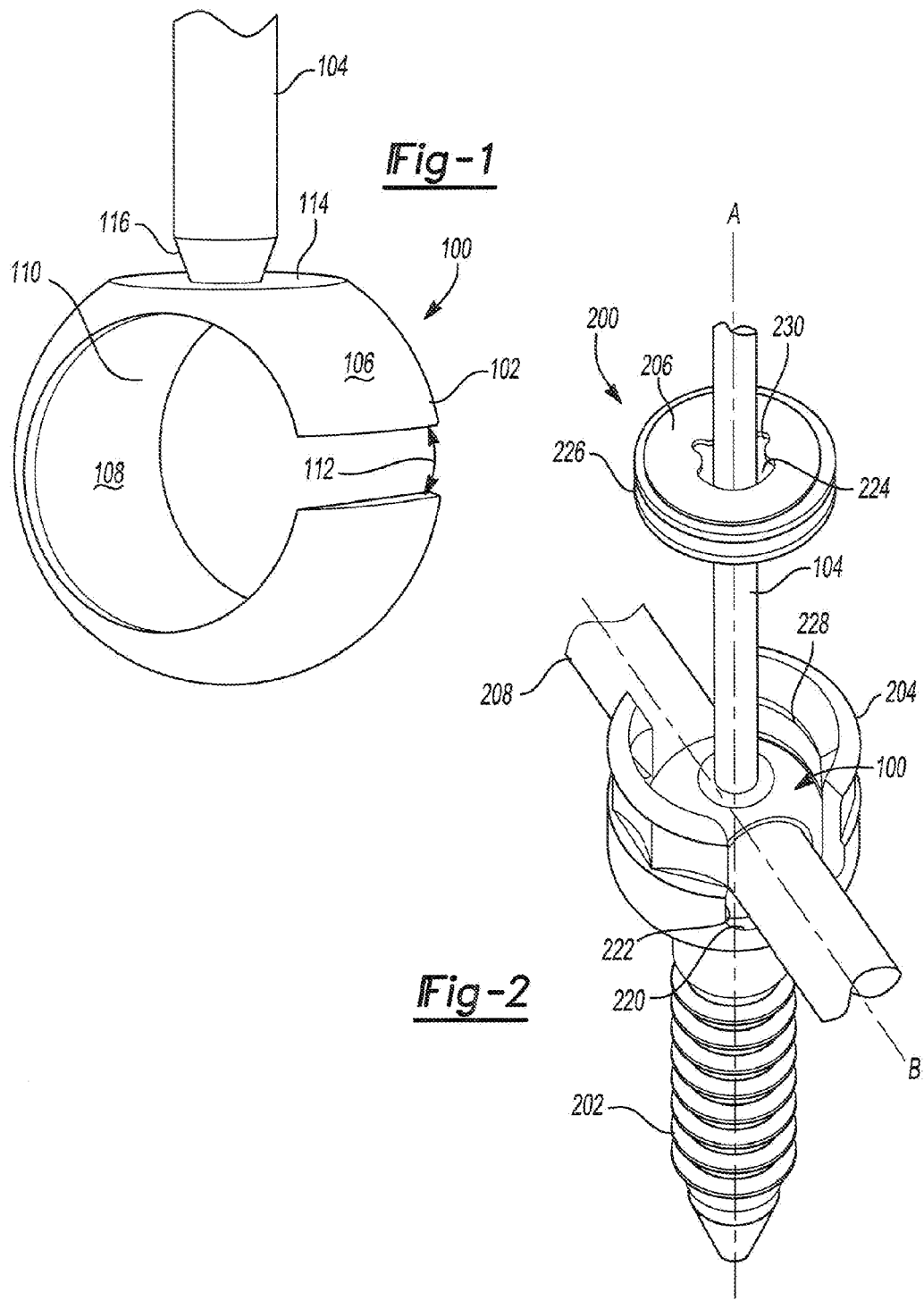

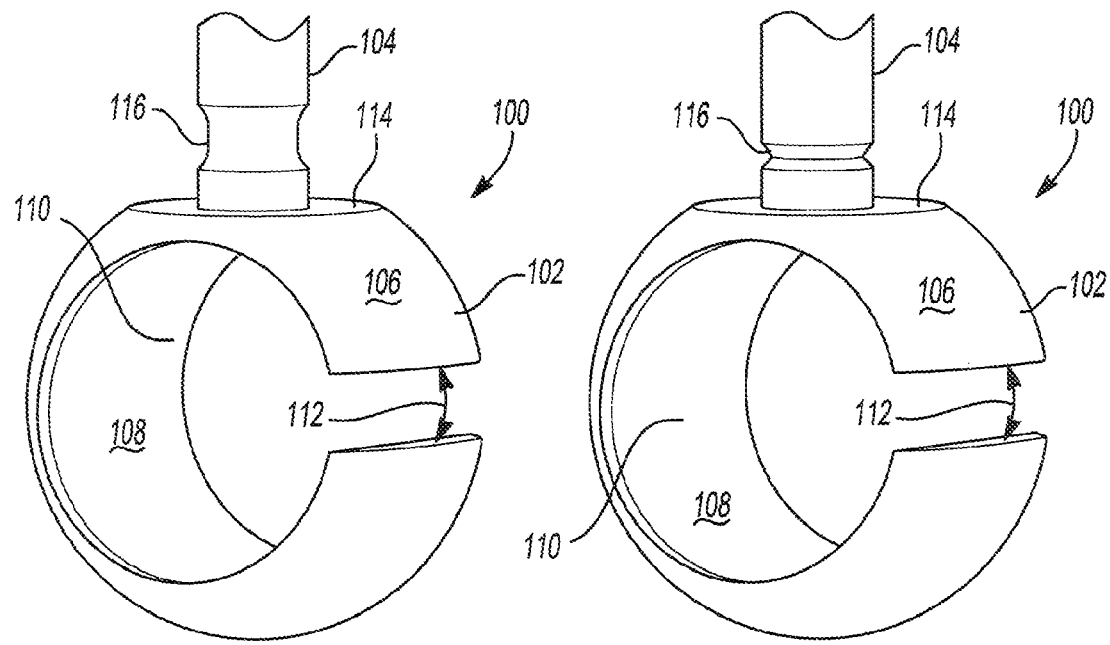
*Fig-3A*  *Fig-3B*
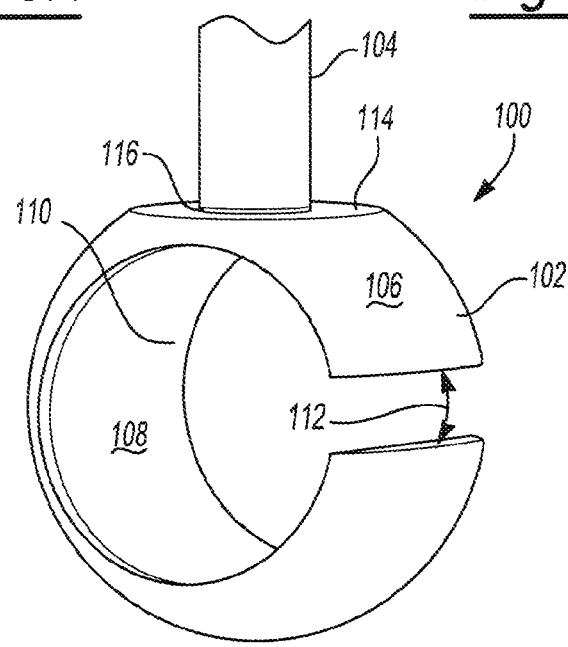
*Fig-3C*

SPINAL FIXATION DEVICE

Various spinal fixation or stabilization devices include pedicle screws having saddle-like receiver portions for receiving and guiding elongated connecting elements between vertebrae. Minimally invasive techniques can be used to reduce the size of incisions and associated trauma for implanting such spinal fixation devices.

The present teachings provide devices and methods of facilitating the insertion and manipulation of connecting elements to spinal fixation devices.

SUMMARY

The present teachings provide an enclosure device for connecting a pedicle fixation device with an elongated spinal fixation member. The enclosure device can include an enclosure member having an outer surface and an internal bore adapted for slidably receiving the spinal fixation member, and an elongated guide member affixed to a portion of the outer surface of the enclosure member. The guide member can have a fracture region for breaking off the guide member from the enclosure member.

The present teachings also provide a pedicle fixation device including a receiver portion defining a transverse opening for an elongated spinal fixation member. The pedicle fixation device can include a resilient enclosure member having an outer surface and an internal bore, and an elongated guide member affixed to a portion of the outer surface of the enclosure member. The enclosure member can be rotatably received within the receiver portion such that the internal bore is aligned with the transverse opening of the receiver portion. The internal bore of the enclosure member can slidably receive the spinal fixation member. The guide member can have a fracture region for breaking off the guide member from the enclosure member.

In another aspect, the present teachings provide a pedicle fixation device that can include a receiver portion defining a transverse opening for receiving an elongated spinal fixation member, an enclosure member having an outer surface, an internal bore and a gap, and an elongated guide member affixed to a portion of the outer surface of the enclosure member. The enclosure member can be rotatably received within the receiver portion such that the internal bore is aligned with the transverse opening of the receiver portion. The guide member can include a fracture region for breaking off the guide member from the enclosure member.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an enclosure device according to the present teachings;

FIG. 2 is a perspective view of an enclosure device according to the presents teachings, shown in a partially assembled pedicle fixation device;

FIG. 3A is a perspective view of an enclosure device according to the present teachings;

FIG. 3B is a perspective view of an enclosure device according to the present teachings;

FIG. 3C is a perspective view of an enclosure device according to the present teachings;

DESCRIPTION OF VARIOUS ASPECTS

Figure 4:
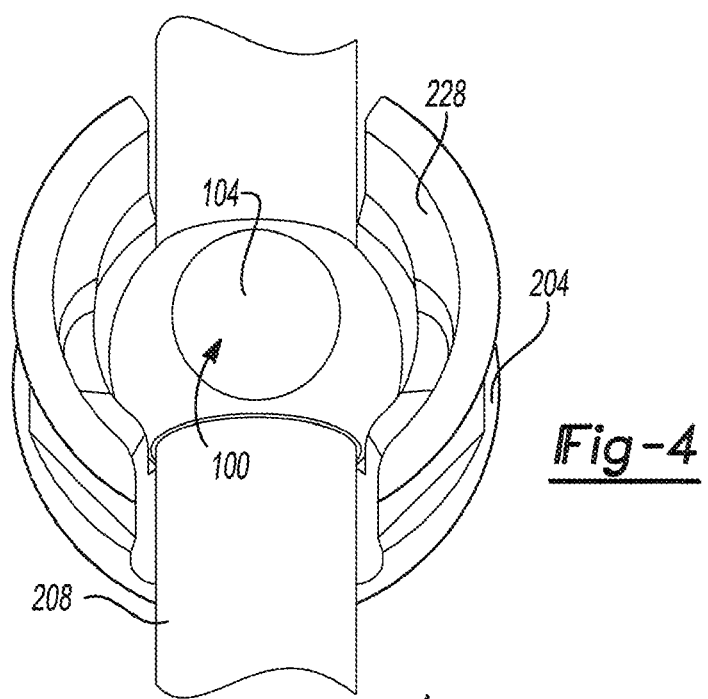
FIG. 4 is a top perspective view of an enclosure device according to the present teachings, shown in a pedicle fixation device.

The following description is merely exemplary in nature and is in no way intended to limit the invention, its application, or uses. For example, although the present teachings are illustrated for pedicle fixation in spinal surgery, the present teachings can be used for other orthopedic applications.

Referring to FIG. 1, an exemplary enclosure device 100 according to the present teachings includes an enclosure member 102 and a guide member 104. The enclosure device 100 can connect a pedicle fixation device 200 with an elongated spinal connecting rod or fixation member 208, as shown in FIG. 2. The pedicle fixation device 200 can be of a conventional type and can include a pedicle screw or fastener 202, and a receiver portion 204. The receiver portion 204 can include a longitudinal opening 220 along a longitudinal axis A, and a transverse opening along a transverse axis B defining a seat for the elongated fixation member 208. The receiver portion 204 can be U-shaped or saddle-shaped. The fastener 202 can be received through the longitudinal opening 220 and can have bone engaging threads or ridges 203.

The enclosure member 102 can be a substantially ball-shaped shell or sleeve having a substantially spherical outer surface 106 and an inner surface 108 defining a cylindrical inner bore 110. The inner bore 110 can be adapted to slidably receive the fixation member 208 when the enclosure device 100 is assembled in the pedicle fixation device 200, as shown in FIG. 2 and described below. The shape of the outer surface 106 can allow the enclosure member 102 to be rotatably received within the receiver portion 204 of the pedicle fixation device 200. The enclosure member 102 can be resilient, for example in the form of a split ring, such that the outer and inner surfaces 106, 108 of the enclosure member 102 are interrupted by a discontinuity or gap 112. The presence of the gap 112 can provide resiliency to the enclosure member 102 for facilitating insertion into the receiver portion 204 and for resiliently compressing the fixation member 208 within the inner bore 110, as described below.

The guide member 104 can be an elongated small diameter element, such as wire. A titanium wire of about 2 mm diameter can be used, for example. The guide member 104 can be fixedly attached to an attachment surface 114 of the enclosure device 102 such that the guide member 104 can extend away from the enclosure device 100 and protrude from the surgical incision or portal. The guide member 104 can be used to install the enclosure device 100 into the pedicle fixation device 200 and control the orientation of the enclosure member 102 relative to the pedicle fixation device 200. The guide member 104 can include a break-off or fracture region 116 adjacent the attachment surface 114 of the enclosure member 102. The fracture region 116 can be a purposefully weakened region of the guide member 104 at or adjacent the transition of the guide member 104 to the attachment surface 114, such that twisting or applying a predetermined amount of torque to the guide member 104 can sever the guide member 104 from the enclosure member 102 at the fracture region 116. Accordingly, the guide member 104 can be removed after the installation and assembly of the enclosure device 100 and the fixation device 200 is completed.

The fracture region 116 can be generally formed as a region of reduced diameter or width of the guide member 104. For example, the fracture region 116 can be defined by a tapered transition to the attachment surface 114, as shown in FIG. 1. The fracture region 116 can also be in the form of a rounded groove or slot, as shown in FIG. 3A. The fracture region 116 can be in the form of a V-shaped or other sharp notch, as shown in FIG. 3B. FIG. 3C illustrates a fracture region 116 located at the connection of the distal end of the guide member 104 to the attachment surface 114. It will be appreciated that the fracture region 116 can have other features that contribute to weakening cross-section. For example, the fracture region 116 can be formed by any means that will produce localized reduction in fracture resistance, including, for example, means that locally weaken the cross-section of the guide member 104 or locally increase stress concentration. Further, weakening can be produced by mechanical means, such as local machining, or means of local chemical erosion, or use of weaker materials at the fracture region 116, and other means. The enclose device 100 can be generally made of polymeric or metal or other biocompatible materials.

Figure 5:
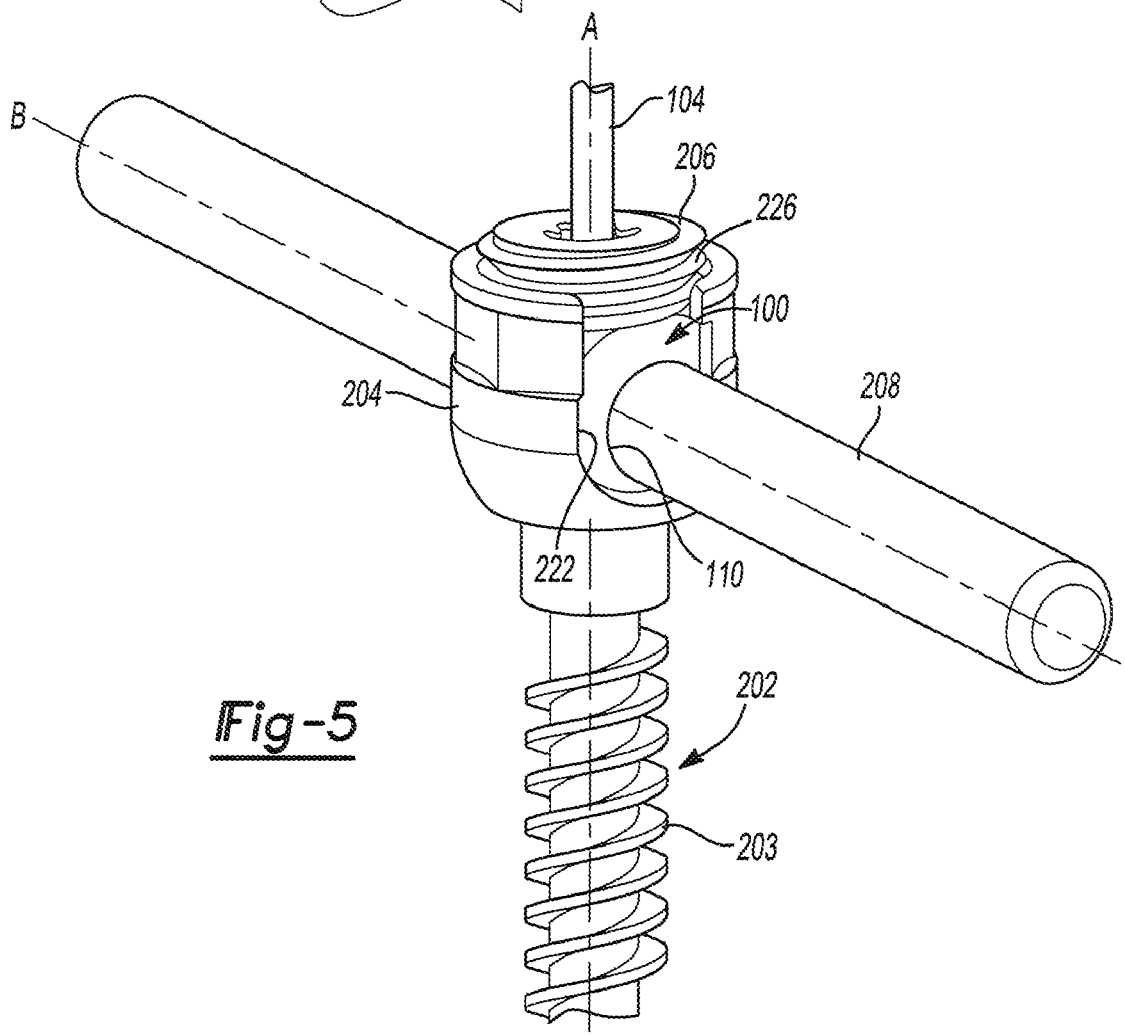
FIG. 5 is a side perspective view of an enclosure device according to the present teachings, shown in a pedicle fixation device.

Referring to FIGS. 2, 4 and 5, the enclosure device 100 can be guided and inserted in the pedicle fixation device 200 using the guide member 104. In one aspect, the enclosure device 100 can be assembled with the elongated fixation member 208, which can be slidably inserted through the cylindrical bore 110 of the enclosure member 102. The enclosure member 102 can be then guided with the guide member 104 into the receiver portion 204 and rotated such that the cylindrical bore 110 is aligned with the transverse opening 222 of the receiver portion 204 allowing the fixation member 208 to be oriented along the transverse axis B. This procedure can be done in connection with a minimally invasive surgical technique. Alternatively, the enclosure device 100 can be first inserted in the receiver portion 204 of the pedicle fixation device 200, the guide member 104 rotated to align the inner bore 110 with the transverse opening 222 of the receiver portion, and then the fixation member 208 can be slidably inserted into the inner bore 110 along the transverse axis B.

A cannulated locking member 206, such as a set screw, can be used to lock the pedicle fixation device 200 with the elongated fixation member 208. The locking member 206 can include a bore 224, such that the locking member 206 can be inserted over the guide member 104 into the receiver portion 204. The locking member 206 can include threading, ridges or other engagement formations 226 for engaging an inner surface 228 of the receiver portion 204 above the fixation member 208 and press down on the enclosure member 102. The enclosure member 104 can deform resiliently such that the gap 112 is reduced and the inner bore 110 tightens around the fixation member 110 securing the fixation member 110 in a locked position. The bore 224 of the locking member 206 can include a driver engagement portion 230 for engaging a driver or other tool that can be used to rotate the locking member 206 to secure the pedicle fixation device 200 with the fixation member 208 in a fixed or substantially rigid configuration, as shown in FIG. 5.

Figure 6:
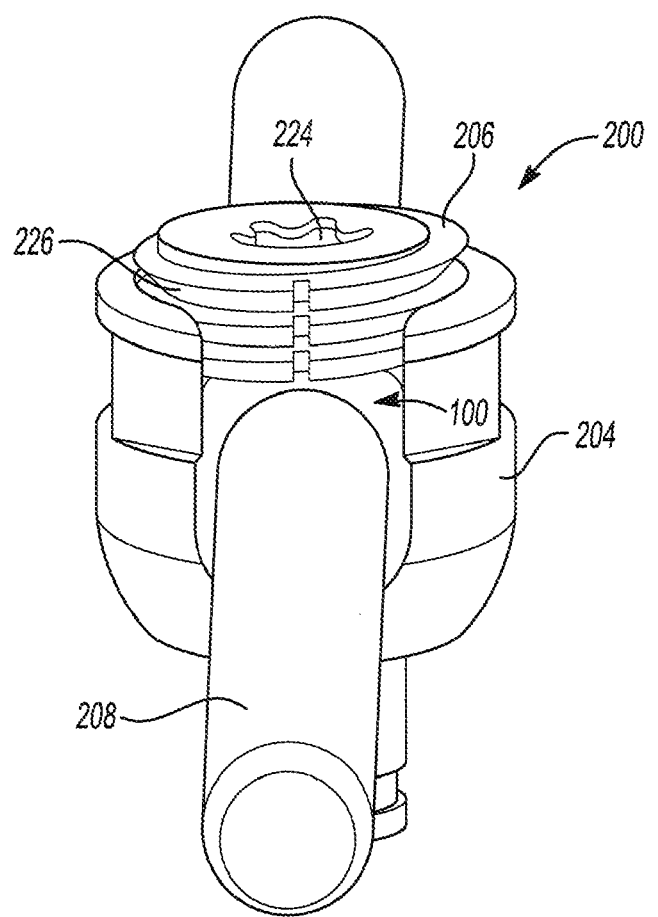
FIG. 6 is a side perspective view of an enclosure device according to the present teachings, shown in a fully assembled pedicle fixation device.

After the pedicle fixation device 200 is fixedly assembled as described above, the guide member 104 can be broken off the enclosure member 102 at the fracture region 116 by applying sufficient torque. The torque can be conveniently applied by using a tool to hold the guide member 104 and apply torsional moment to the guide member 104 relative to attachment surface 114. The fracture region 116 can be dimensioned such that when the guide member 104 breaks off at the fracture region 116, the portion of the guide member 104 that remains attached to the enclosure member 102 between the attachment surface 114 and the fracture region 116 is fully contained within the bore 224 of the locking member 206 and does not protrude above the locking member 206, as shown in FIG. 6.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An enclosure device for connecting a pedicle fixation device with an elongated spinal fixation member, the enclosure device comprising:
   an enclosure member having an outer surface and an internal bore adapted for slidably receiving the spinal fixation member, the enclosure member received within a U-shaped receiver portion of the pedicle fixation device; and
   an elongated guide wire having a terminal end fixedly attached to a portion of the outer surface of the enclosure member to guide the enclosure member into the pedicle fixation device, the guide wire having a fracture region for breaking off the guide wire from the enclosure member, the fracture region dimensioned such that the portion of the guide wire that remains attached to the enclosure member after the guide wire breaks from the enclosure member is fully contained within the pedicle fixation device.

2. The enclosure device of claim 1, wherein the fracture region is a region of reduced cross-section of the guide wire.

3. The enclosure device of claim 1, wherein the fracture region is a region of reduced fracture resistance in torsion of the guide wire.

4. The enclosure device of claim 1, wherein the fracture region is a region of increased stress concentration in torsion of the guide wire.

5. The enclosure device of claim 1, wherein the fracture region is defined by rounded groove in the guide wire.

6. The enclosure device of claim 1, wherein the fracture region is defined by sharp notch in the guide wire.

7. The enclosure device of claim 1, wherein the fracture region is adjacent to enclosure member.

8. The enclosure device of claim 1, wherein the outer surface of the enclosure member is substantially spherical.

9. The enclosure device of claim 8, wherein the internal bore is cylindrical.

10. The enclosure device of claim 1, wherein the enclosure member is resilient and includes a gap.

11. A pedicle fixation device comprising:
    a U-shaped receiver portion having a transverse opening formed from a proximal-most end of the receiver portion to an area adjacent to a distal end of the receiver portion;
    a resilient enclosure member having an outer surface and an internal bore, the enclosure member rotatably received within the receiver portion such that the internal bore is aligned with the transverse opening of the receiver portion, the internal bore slidably receiving a spinal fixation member; and
    an elongated guide wire having a terminal end fixedly attached to a portion of the outer surface of the enclosure member for guiding the enclosure member into the receiver portion, the guide wire having a fracture region for breaking off the guide wire from the enclosure member.

12. The pedicle fixation device of claim 11, wherein the outer surface of the enclosure member is substantially spherical and the internal bore of the enclosure member is cylindrical.

13. The pedicle fixation device of claim 12, wherein the fracture region is a V-shaped notch.

14. A pedicle fixation device comprising:
- a U-shaped receiver portion defining a transverse opening for receiving an elongated spinal fixation member;
- an enclosure member having an outer surface, an internal bore and a gap, the enclosure member rotatably received within the receiver portion such that the internal bore is aligned with the transverse opening of the receiver portion;
- an elongated guide wire having a terminal end fixedly attached to a portion of the outer surface of the enclosure member to guide the enclosure member into the receiver portion, the guide wire comprising a fracture region for breaking off the guide wire from the enclosure member; and
- a cannulated locking member engageable with an inner surface of the receiver portion above the enclosure member, the locking member defining a bore, the guide wire passable through the bore of the locking member,
- wherein the fracture region is dimensioned such that the portion of the guide wire that remains attached to the enclosure member after the guide wire breaks off is fully contained within the bore of the locking member.

15. The pedicle fixation device of claim 14, further comprising an elongated fixation member slidably received through the internal bore of the enclosure member and extending along the transverse opening of the receiver portion.

16. The pedicle fixation device of claim 14, wherein the outer surface of the enclosure member is substantially spherical.

17. The pedicle fixation device of claim 16, wherein the internal bore of the enclosure member is cylindrical.

18. The pedicle fixation device of claim 17, wherein the fracture region is a V-shaped notch.

19. The pedicle fixation device of claim 14, wherein the receiver portion defines and a longitudinal opening, and further comprising a pedicle fastener passing through the longitudinal opening.

* * * * *